United States Patent [19] [11] Patent Number: 5,823,974
Grassi [45] Date of Patent: Oct. 20, 1998

[54] BIOMEDICAL APPARATUS PARTICULARLY FOR MEASURING ANISOMELIA OF THE LOWER LIMBS

[75] Inventor: Silvano Grassi, Biadene Di Montebelluna, Italy

[73] Assignee: Sponsor S.r.l., Biadene Di Montebelluna, Italy

[21] Appl. No.: 591,520

[22] PCT Filed: Jun. 16, 1995

[86] PCT No.: PCT/EP95/02340

§ 371 Date: Feb. 6, 1996

§ 102(e) Date: Feb. 6, 1996

[87] PCT Pub. No.: WO95/35063

PCT Pub. Date: Dec. 28, 1995

[30] Foreign Application Priority Data

Jun. 17, 1994 [IT] Italy .................................. PD94A0112
Dec. 30, 1994 [IT] Italy .................................. PD94A0227

[51] Int. Cl.⁶ .................................................. A61B 5/103
[52] U.S. Cl. ........................................... 600/595; 600/594
[58] Field of Search .................................... 128/774, 779, 128/781, 782; 600/594, 595

[56] References Cited

U.S. PATENT DOCUMENTS

| 2,043,187 | 6/1936 | Owens | 128/779 |
| 4,033,329 | 7/1977 | Gregory | 128/781 |
| 4,425,713 | 1/1984 | Rotella | 128/774 X |
| 4,802,494 | 2/1989 | Gardiner | 128/782 X |
| 4,928,708 | 5/1990 | Landwehr | 128/774 X |
| 5,285,022 | 2/1994 | Antone | 128/774 X |
| 5,474,086 | 12/1995 | McCormick | 128/782 |
| 5,490,518 | 2/1996 | Russo | 128/774 |

FOREIGN PATENT DOCUMENTS

| 2491754 | 4/1982 | France . | |
| 2647331 | 11/1990 | France | 128/772 |
| 1920766 | 11/1970 | Germany . | |
| 4429114 | 4/1995 | Germany . | |
| 3202443 | 1/1984 | Netherlands | 128/774 |
| 825000 | 4/1981 | U.S.S.R. | 128/774 |
| 0904663 | 2/1982 | U.S.S.R. | 128/782 |
| 1423112 | 9/1988 | U.S.S.R. | 128/774 |

*Primary Examiner*—Richard J. Apley
*Assistant Examiner*—William LaMarca
*Attorney, Agent, or Firm*—Guido Modiano; Albert Josif; Daniel J. O'Byrne

[57] ABSTRACT

A biomedical apparatus, particularly for measuring anisomelia of the lower limbs of a patient and the posture of the trunk of the patient in relation to the measured anisomelia. The apparatus comprises at least one first post extending vertically from an apparatus for evaluating anisomelia of the lower limbs, and at least one postural geometry measurement device is slidingly coupled to the first post.

16 Claims, 5 Drawing Sheets

BIOMEDICAL APPARATUS PARTICULARLY FOR MEASURING ANISOMELIA OF THE LOWER LIMBS

BACKGROUND OF THE INVENTION

The present invention relates to a biomedical apparatus articularly for measuring the posture of a patient's trunk in relation to anisomelia (unequal length) of the lower limbs.

Apparatuses for evaluating anisomelia of the lower limbs are known.

Despite their various embodiments, these apparatuses substantially comprise two platforms that are independent one from another, are mounted on a common base and can sink vertically when loaded.

Sinking of the platforms is currently achieved by resting each platform on a flexible means such as a block made of flexible foamed plastics.

The platforms cooperate with means for positioning the lumbosacral line of the patient vertically with respect to the median foot resting line, and with anisomelia measurement means.

The positioning and measurement means are commonly provided as sliders that can move along an appropriate structure for coccygeal and cervical centering along a common vertical line.

The positioning and measurement means furthermore comprise a graduated scale acting as an accessory of the apparatus.

Although it has proved to be technically rather effective, the above mentioned apparatus has been found to be affected, in practice, by some drawbacks that are mainly due to the fact that the sinking of the platforms is achieved by means of said blocks made of flexible foamed material.

It is in fact necessary to have a range of blocks of different densities to be replaced beneath the platforms, so as to adapt the system to the loading conditions, which are of course different for different patients according to their weight.

Finally, the need to replace the blocks when the patient changes makes anisomelia evaluation troublesome, also in view of the fact that the new blocks must be chosen by trial and error.

Furthermore, in these apparatuses for measuring the anisomelia of the lower limbs, the patient, who is indeed affected by said anisomelia, is placed on the apparatus by making him stand on the platforms and making him assume a position in which the line connecting the coccyx and the cervix is truly vertical.

However, if anisomelia is not measured while the patient is in a perfectly straight position, that is to say, while the coccygeosacral line is substantially perpendicular with respect to the ground and with no torsions of the pelvis, the measurement of the anisomelia is altered, since the skeletal system of the patient tends to compensate by possibly worsening the curve of the spinal column.

Furthermore, with currently commercially available models, it is almost impossible to perform an overall evaluation of the postural geometry induced by the apparatus for evaluating postural dysfunctions, both in a free posture, for mere evaluation, and when controlled in preset positions in order to evaluate by feedback the effects induced on the patient's posture.

SUMMARY OF THE INVENTION

The aim of the present invention is to provide a biomedical apparatus particularly for checking postural dysfunctions, which in addition to allowing to measure the postural geometry when the patient is placed on devices for evaluating anisomelia of the lower limbs, also allows an overall evaluation of the postural behavior of the skeleton of the patient subjected to preset conditionings.

Within the scope of this aim, a consequent primary object is to provide an apparatus for evaluating anisomelia of the lower limbs that eliminates the above described drawbacks in known types.

Another object of the present invention is to provide a biomedical apparatus the structure whereof can be easily adapted to the requested measurement needs and can support and integrate various auxiliary devices for measuring particular postural geometries.

Another object of the present invention is to provide a biomedical apparatus that is highly reliable in measurement and can be integrated with data processing and transducing means of the electric and electronic type.

Another object of the present invention is to provide a biomedical apparatus that can be manufactured with known technologies and in which the costs are convenient for the field of use.

Another object of the present invention is to provide a biomedical apparatus in which completeness in measurement does not negatively affect simplicity in use and maintenance.

This aim, these objects, and others which will become apparent hereinafter are achieved by a biomedical apparatus, particularly for measuring the posture of the trunk of a patient in relation to anisomelia of the lower limbs, characterized in that it comprises at least one first post extending vertically from an apparatus for evaluating the anisomelia of the lower limbs, at least one postural geometry measurement device being slidingly coupled to said post.

Advantageously, said apparatus for evaluating anisomelia of the lower limbs, of the type comprising two independent movable platforms that can sink vertically when loaded and cooperate with means for positioning the lumbosacral line of the patient vertically with respect to the median foot resting line and with anisomelia measurement means, is characterized in that each one of said platforms is mounted on at least one respective pneumatic actuator that achieves sinking by adjusting the internal pressure.

BRIEF DESCRIPTION OF THE DRAWINGS

Further characteristics and advantages of the invention will become apparent from the detailed description of an embodiment thereof, illustrated only by way of non-limitative example in the accompanying drawings, wherein.

DESCRIPTION OF THE PREFERRED EMBODIMENTS

Figure 1:
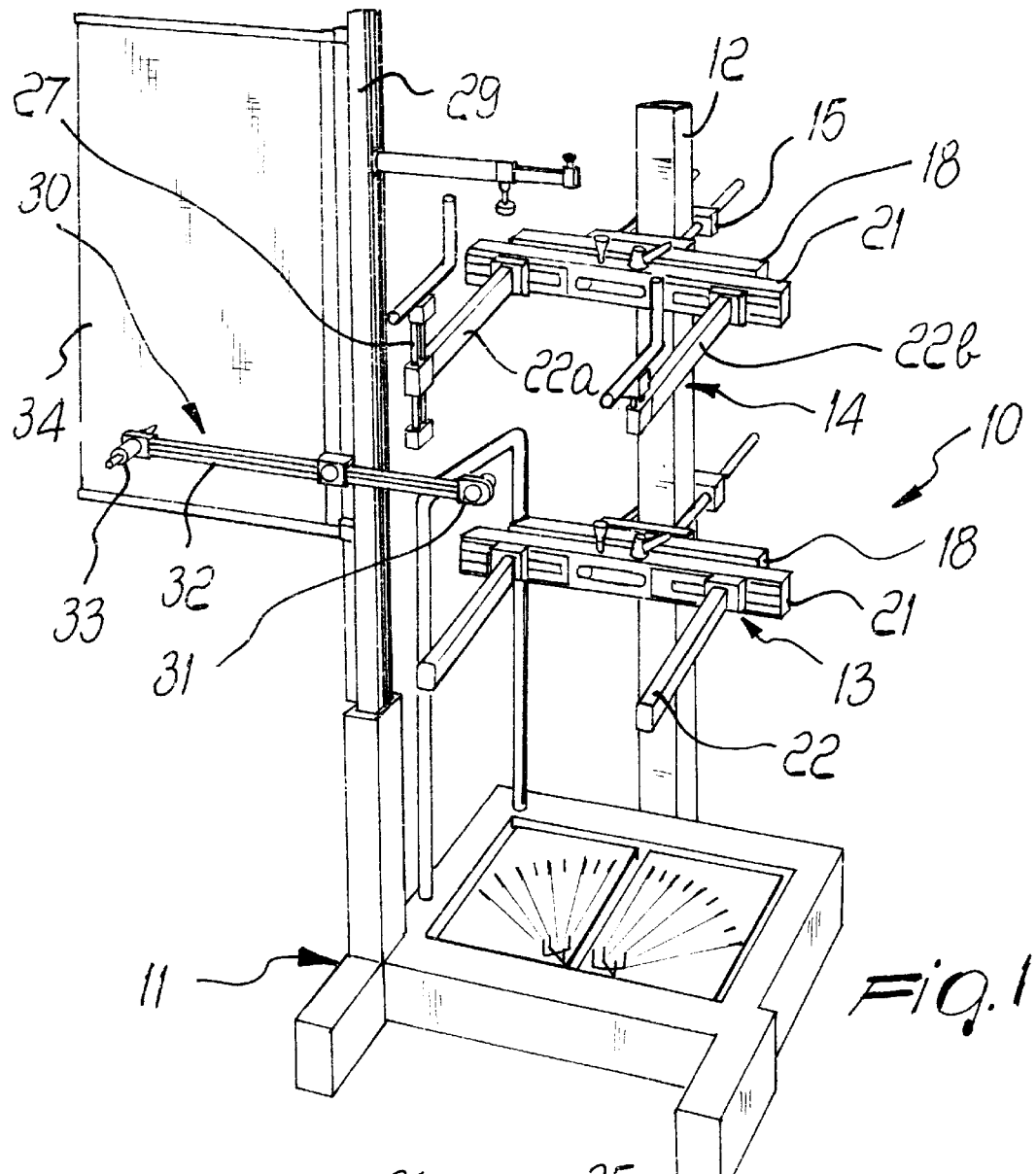
FIG. 1 is an overall axonometric view of the biomedical apparatus according to the invention.
Figure 2:
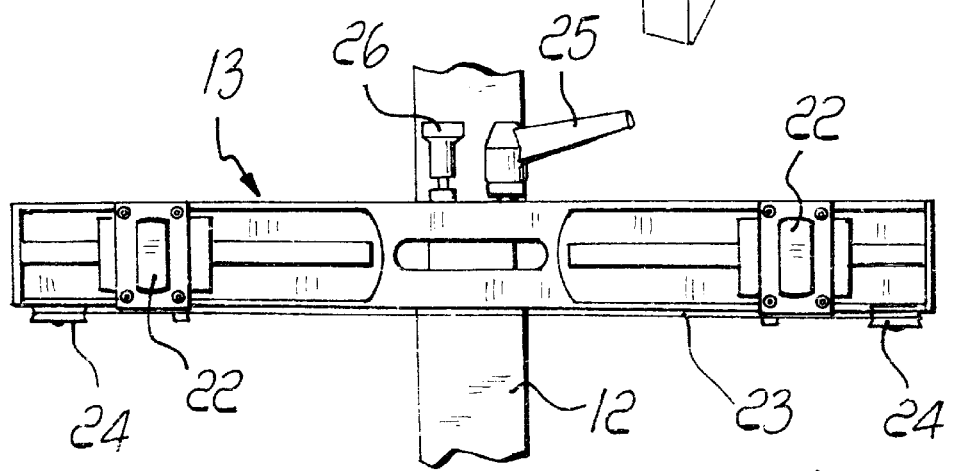
FIG. 2 is a front view of a first detail of the biomedical apparatus according to the invention.
Figure 3:
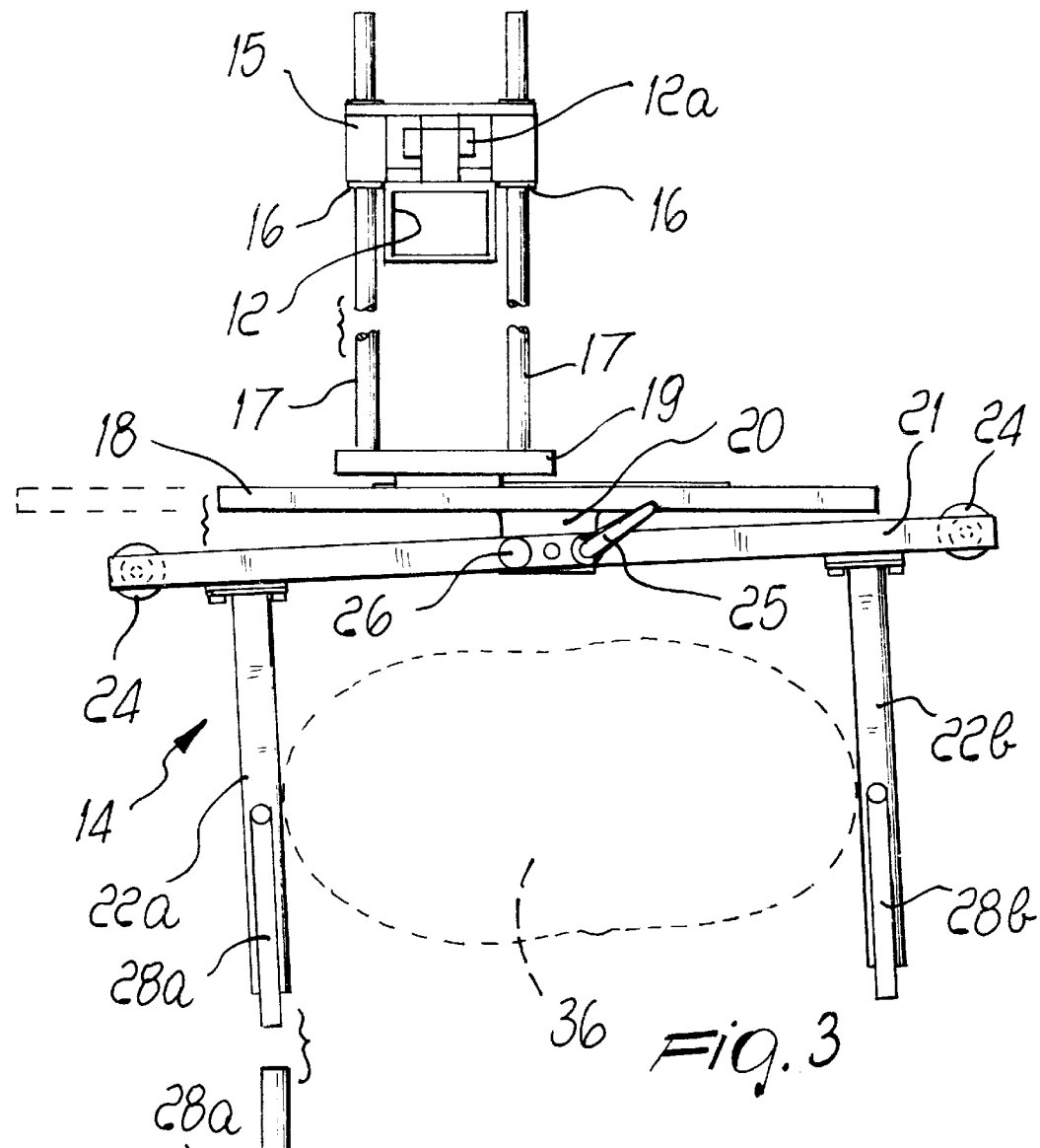
FIG. 3 is a top view of a second detail related to FIG. 2.
Figure 4:
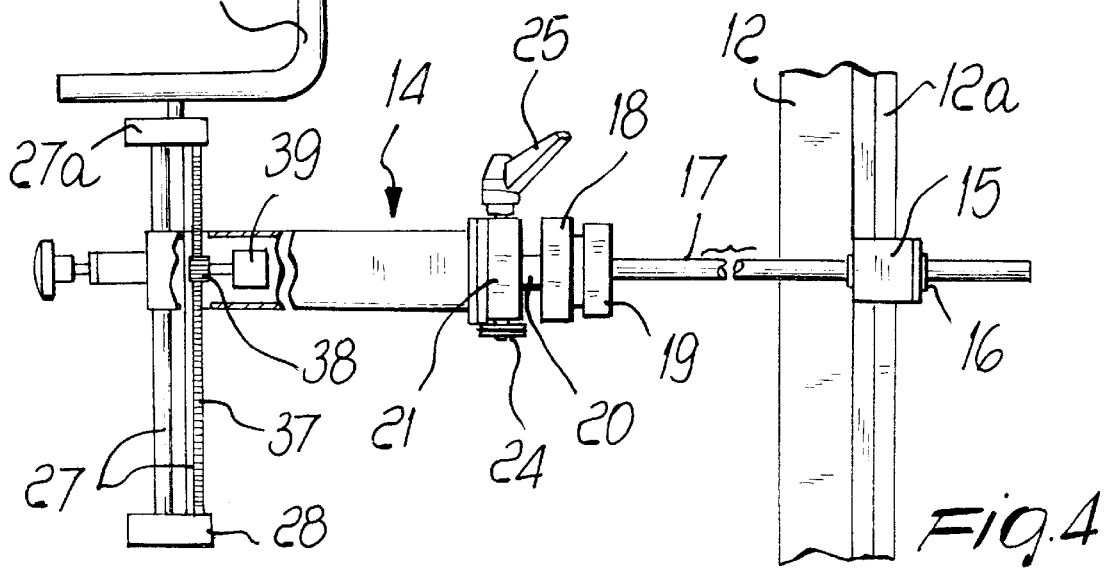
FIG. 4 is a side view of the detail related to figure 3.
Figure 5:
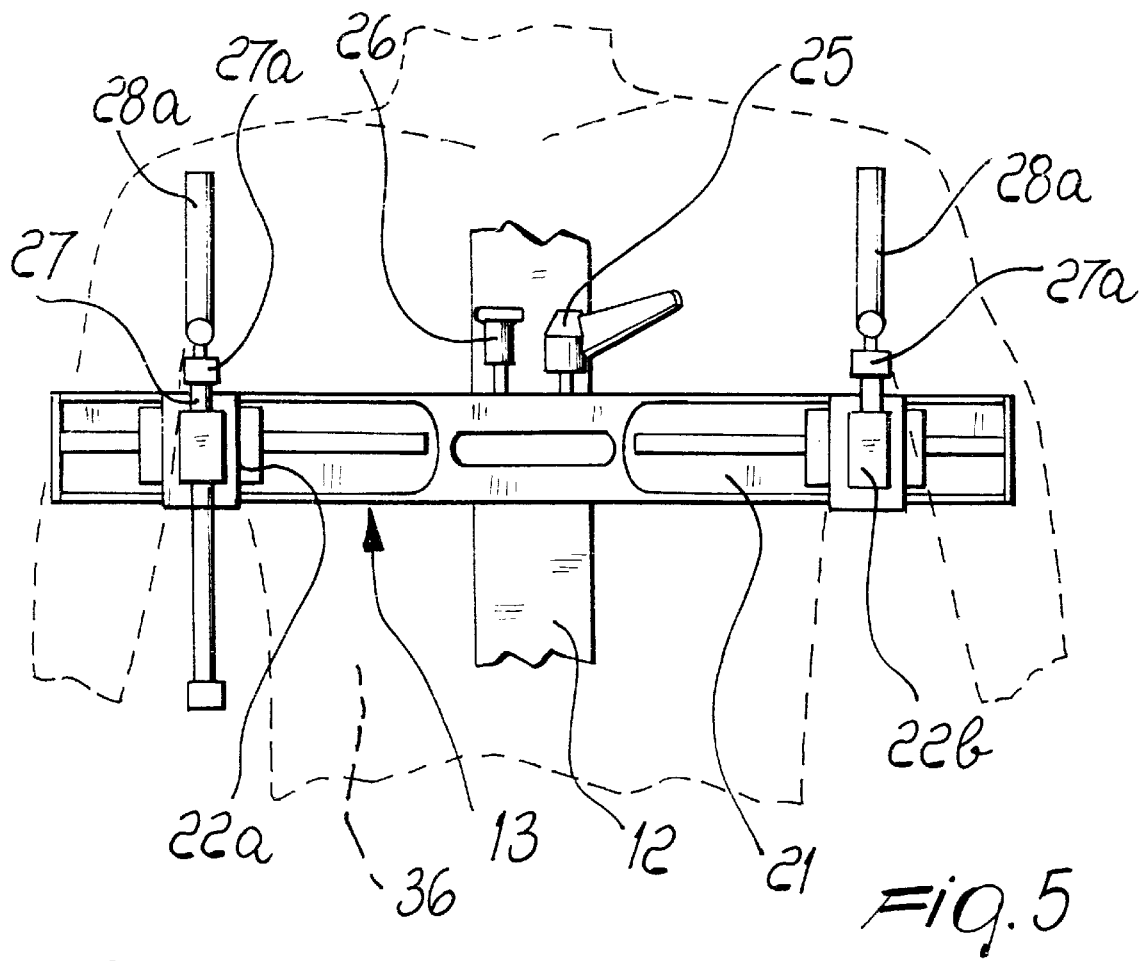
FIG. 5 is a front view of the detail of FIG. 3.

With particular reference to FIGS. 1 to 7, a biomedical apparatus, particularly for measuring the posture of the trunk of a patient in relation to anisomelia of the lower limbs, according to the invention, is generally designated by the reference numeral 10.

The apparatus 10 comprises a first post 12 extending vertically from an apparatus for evaluating anisomelia of the lower limbs, generally designated herein by the reference numeral 11; two devices for measuring postural geometry, designated herein by the reference numerals 13 and 14 respectively, are slidingly coupled to said first post 12 by means of guides with sliders or cursors 12a of the ballscrew type of a per se known type that are formed longitudinally with respect to said first post 12.

Before proceeding with the description, it is specified that the first post 12 is fixed to the apparatus for evaluating anisomelia of the lower limbs 11 in such a manner that, when the patient is in place, said first post is arranged substantially in front of the patient.

The measurement device 13 substantially comprises a slider 15, which slides along the first post 12 and to which two parallel rods 17, which in this case have a circular cross-section, are slidingly coupled by means of through holes 16 of said slider; said rods 17 constitute translatory motion means for a first rod-like element 18.

More specifically, the rods 17 are arranged so that they slide within the through holes 16 in a direction that is substantially perpendicular to the first post 12 and substantially parallel to the front/back directrix of the patient placed on the apparatus for evaluating anisomelia of the lower limbs 11.

A plate 19 is fixed at the ends of the rods 17 that are connected to the apparatus 11, and the first rod-like element 18 is slidingly coupled to said plate by means of a ballscrew guide applied therein.

The first rod-like element 18 slides with respect to the plate 19 along a direction that is substantially perpendicular to the direction of motion of the rods 17 and lies on a plane that is substantially perpendicular to the first post 12.

A bracket 20 lies in a median region of the first rod-like element 18, and a second rod-like element 21 is pivoted to said bracket along a substantially vertical rotation axis at a median region.

Said second rod-like element 21 thus oscillates on a plane that lies at right angles to the first post 12.

The ends of two substantially rod-like arms 22 are furthermore slidingly coupled to said second rod-like element 21 and can move at right angles to the direction of their longitudinal extension and on a plane that coincides with, or is parallel to, the oscillation plane of said second rod-like element 21.

The two arms 22 are furthermore parallel and equal in length.

Furthermore, the two arms 22 also move with respect to the second rod-like element 21 by means of ballscrew guides applied therein, and their movements are linked to each other, since their sliding ends are connected to a common cable 23 that is stretched between two pulleys 24.

The two pulleys 24 are rotatably coupled below the second rod-like element 21 and cause an opening movement of one of the two arms 22 to be matched by a corresponding symmetrical opening movement of the other arm 22.

Furthermore, as regards the second rod-like element 21, means for locking its oscillation are arranged thereon and are constituted in this case by locking levers, respectively designated by the reference numerals 25 and 26.

As regards the measurement device 14, it is substantially identical to the measurement device 13, and therefore reference is made to the above description regarding the measurement device 13 for the numbering of its components.

However, a means for measuring the difference in level between the shoulders is fixed to the free end of one of the two arms 22 of the measurement device 14; said means is constituted, in this case, by a third rod-like element 27 sliding in the said end, and a block 28 is fixed to one end of said third rod-like element 27, as also occurs on the other arm, and supports a rod-like element 28a having an L-shaped cross-section for resting and centering the armpits.

The third rod-like element comprises a ring, not shown in the figures, with a gear that is fixed to the stem of a potentiometer inserted in the arm 22.

The apparatus 10 furthermore comprises a second post 29 that extends from the apparatus for evaluating the dysfunction of the lower limbs 11; when the patient is in place, said second post is substantially arranged laterally and to the rear with respect to said patient.

The second post 29 furthermore supports a pantograph, generally designated herein by the reference numeral 30, which includes an element for tracing the extension line of the spinal column 31 connected, by means of rods 32, to a pen 33 that reproduces the shape on a board 34.

Figure 6:
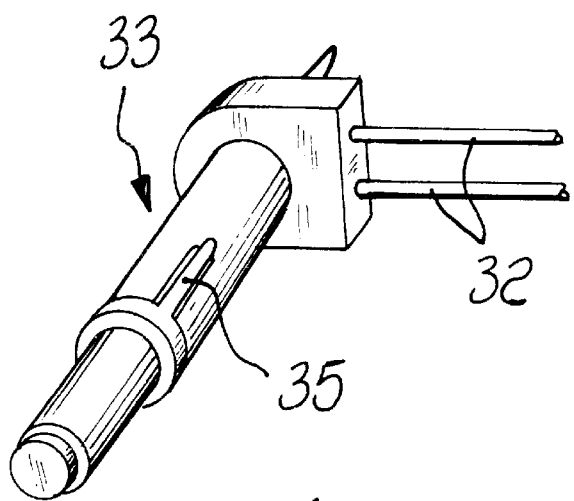
FIGS. 6 and 7 are two axonometric views, in two different operating configurations, of another detail of the biomedical apparatus according to the invention.
Figure 7:
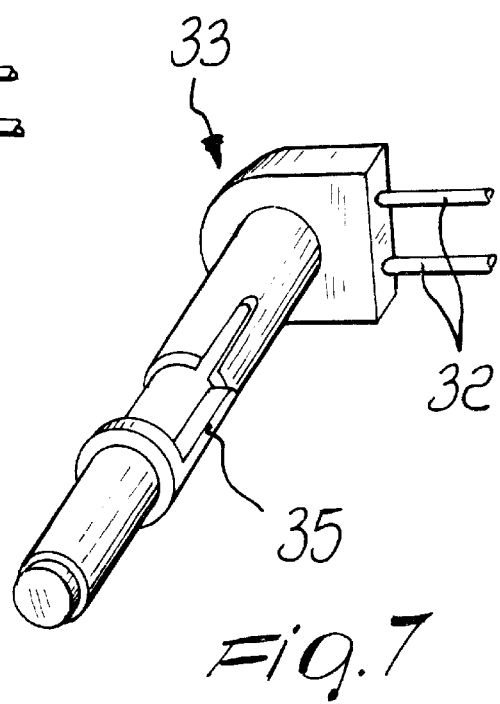
Figure 8:
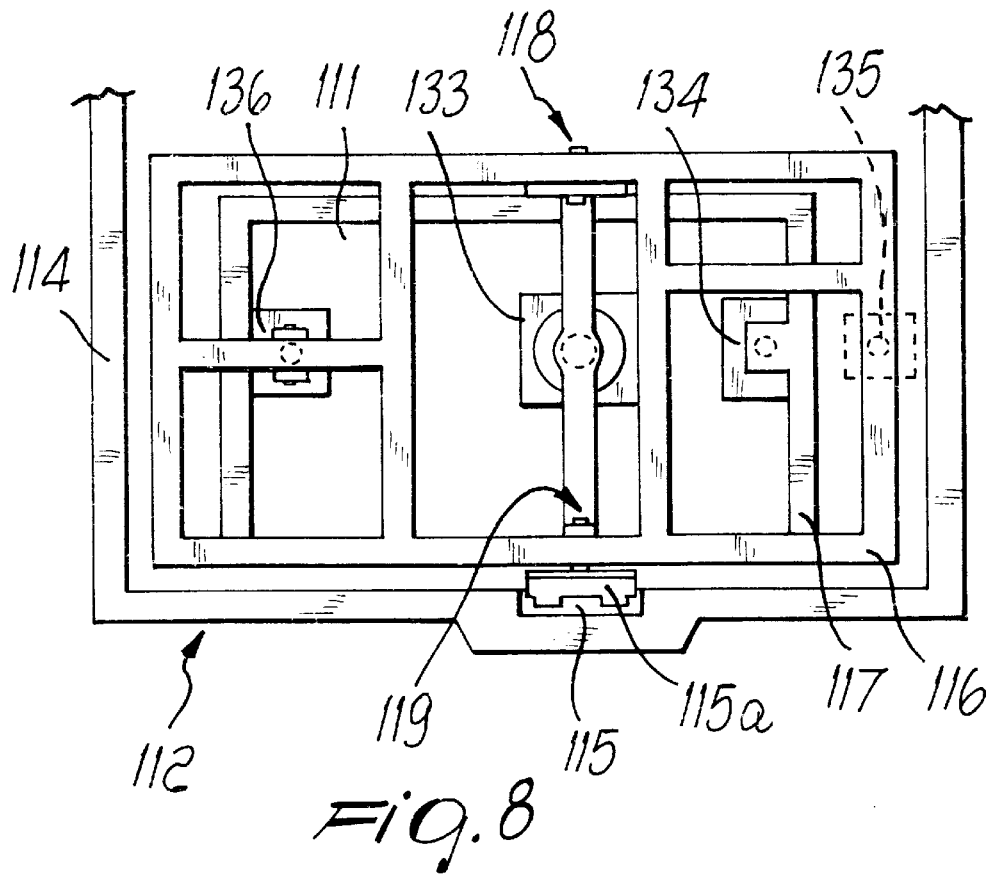
FIG. 8 is a top view of one of the platforms of the apparatus of FIG. 1.
Figure 9:
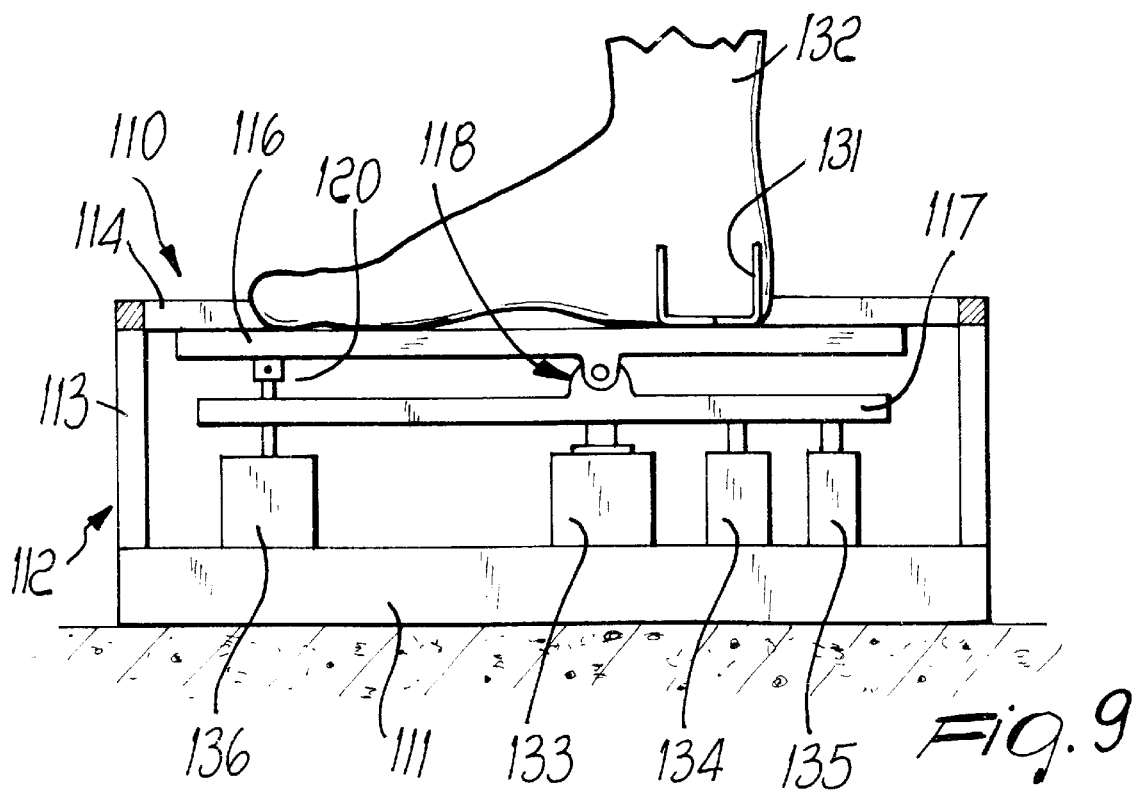
FIG. 9 is a side view of the platform of FIG. 8.
Figure 10:
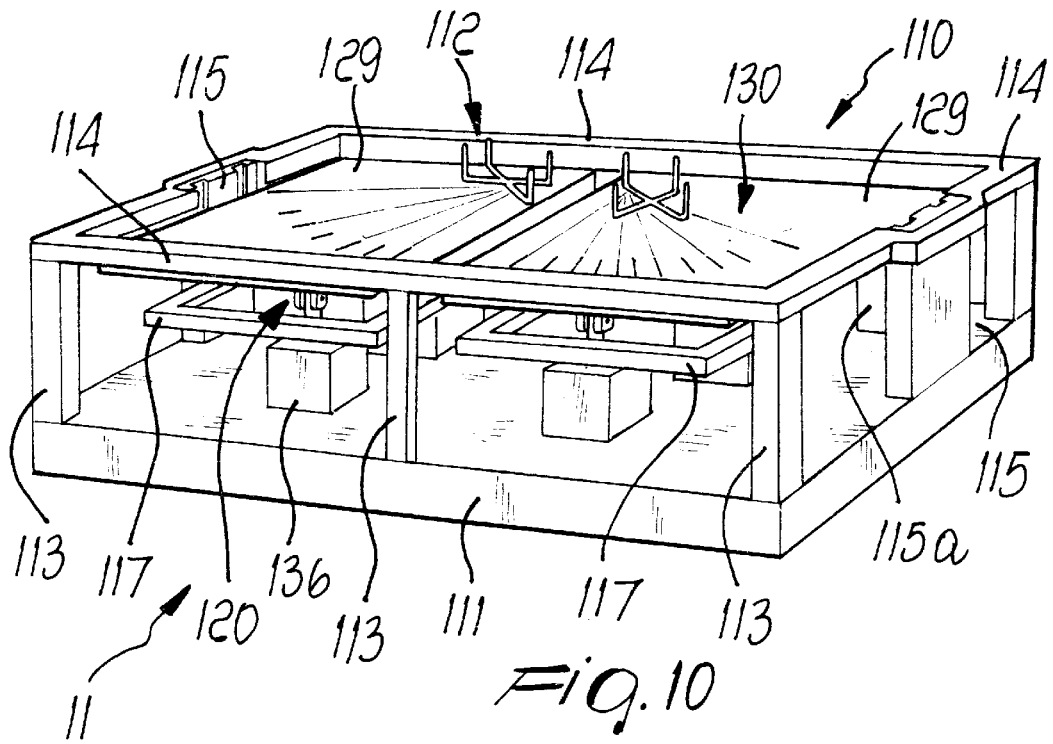
FIG. 10 is a perspective view of the anisomelia measurement apparatus.
Figure 11:
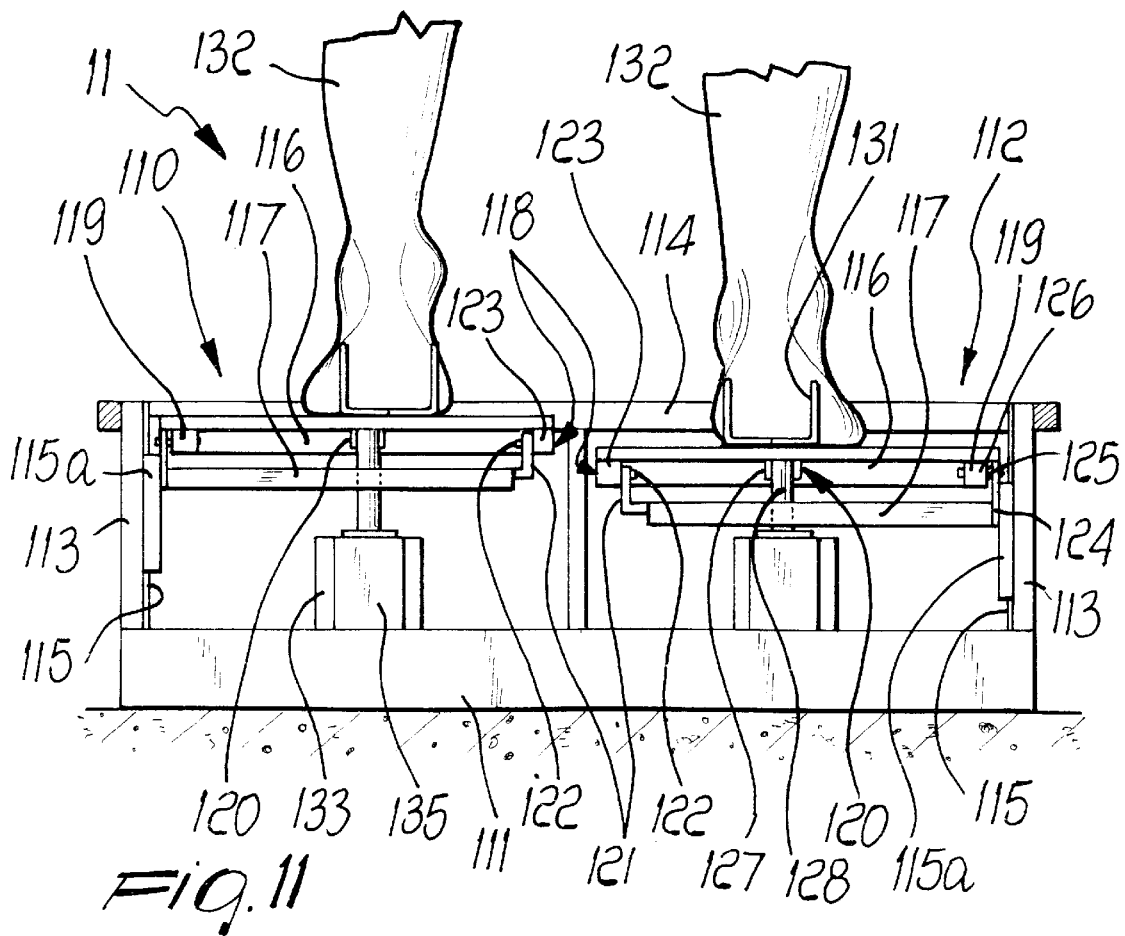
FIG. 11 is a front view of the apparatus of FIG. 10 during use.

The pen 33, as clearly shown by FIGS. 6 and 7, can be easily activated or deactivated by simple rotation and by means of cams 35.

Measuring and transducing means are present in this case and are not shown in the figures; said means comprise potentiometers that can be advantageously connected to means for the computerized processing of data.

The apparatus 10 furthermore includes an alarm device, also not shown in the figures, for reporting any anomalies with respect to a preset routine procedure.

With reference to the above mentioned FIGS. 8 to 11, the apparatus 11 for measuring anisomelia comprises a footing 111 shaped substantially as a rectangular parallelepiped, with a supporting frame 112 extending from the upper surface thereof.

The supporting frame 112 comprises six vertical uprights 113 arranged in groups of three along opposite sides of the footing 111, four crosspieces 114 parallel to the footing 111 being further mounted on top of the uprights.

For the sake of clarity in description, it is stated that any element extending in a direction that lies substantially at right angles to the footing 111 will be described as vertical.

In a central zone of each of the sides adjacent the sides along which the uprights 113 are located, two linear ballscrew guides 115 extend from the footing 111.

The two guides 115 are self-aligned and have vertical parallel axes aligned according to a direction substantially parallel to the sides along which the uprights 113 are located.

On each of the two guides 115 slide, both by means of a slider 115a, a first frame 116 and a second frame 117.

The first frame 116 and the second frame 117 are connected therebetween by two coaxial hinges 118, 119 having rotation axes substantially parallel to the base 111 and to the alignment direction of the guides 115.

The hinges 118 and 119 are located at a central zone with respect to the lateral edges of the first frame 116 and of the second frame 117.

In particular, the hinge 118 is made from a L-shaped plate rigidly connected to the second frame 117 and having a free end holed and pivoted by means of a pivot 122 rigidly connected to a tab 123 of the first frame 116.

The hinge 119 is made from a plate 124 rigidly connected to the slider 115a and to the second frame 117 while a pivot 125 welded thereon is pivoted to a tab 126 of the first frame 116.

On the upper surface of each of the first frames 116 a platform 129 is fixed on which locator graduations 130 are provided for the correct symmetrical position of the divarication of the feet 132.

Respective heel units 131 for the exact placement of the feet 132 are further located also on the platforms 129.

Each one of the second frames 117 is mounted on a respective pneumatic piston 133 to achieve sinking of the platforms, on a respective pneumatic locking piston 134, and on a respective potentiometer 135 for the reading of the differences in limb length.

The pistons 133, the pistons 134, and the potentiometers 135 corresponding to the related second frames 117 all extend vertically from the footing 111.

Furthermore, considering only the second frames 117, the respective pistons 133 and 134 and the potentiometers 135 have vertical axes all lying on a single plane.

Other pneumatic pistons 136 extend from the footing 111, and their stems pass through the respective second frames 117 and anchor below each corresponding first frames 116 through a hinge 120.

The hinge 120 is made of two tabs 127 parallel to each other and rigidly connected to the first frame 116, a free end 128 of the relative pneumatic piston 136 being pivoted therebetween.

A circuit of ducts for feeding the pistons 133, 134 and 136 is provided and is not shown for the sake of simplicity.

In practice, the operation of the biomedical apparatus is as follows: when the patient, designated herein by the reference numeral 36, is placed on the apparatus for evaluating anisomelia of the lower limbs 11, by means of an appropriate adjustment and positioning on said patient of the measurement devices 13 and 14, it is possible to measure the posture of a patient with reference to the anisomelia of the lower limbs, relative to the shoulders of the patient 36 and relative to his pelvis.

Furthermore, for a measurement that, in addition to being documented numerically, must also be documented graphically, it is possible to use the pantograph, which can produce, even in full scale, the shape of the spinal column in order to perform appropriate adjustments and corrections of the posture of the patient.

When the patient is placed sideways, this pantograph can also trace any lordosis or kyphosis.

These operations can be further automated by virtue of interfacing with the measuring, transducing, and processing means of the electric, electromechanical, and electronic type as well as by virtue of computerized means of a per se known type.

Anisomelia can be measured as follows: the pistons 133 are subjected to an internal pressure that is greater than the load produced by the weight of the patient.

In this condition, the first frames 116 and thus the platforms 129 are fully raised, co-planar, and locked by the activation of the pistons 134.

After positioning the patient affected by anisomelia so that his feet 132 are on the platforms 129, the patient is placed so that his lumbosacral line is vertical with respect to the median foot resting line.

This is performed by means of known coccygeal and cervical centering sliders that are per se known and are not illustrated in the figures.

Once the pistons 134 have been deactivated, the pressure inside the pistons 133 is reduced simultaneously to values that achieve the descent of the platforms 129.

This descent will be different due to the different loading conditions of the two feet caused by the anisomelia, and there will be a difference in level between the two platforms.

When this descent level difference remains constant, the pressure inside the pistons 133 is blocked and, by means of the potentiometers 135 and corresponding known transducing arrangements, it is possible to read on a display the difference between the two levels constituting the anisomelia of the patient.

It should also be noted that the pistons 136 allow to adjust the height of the heels with respect to the remaining front parts of the feet.

It is possible to set, by means of the pistons 133, different postures (forced positions) for observing the behaviour of the backbone or of the postures in general.

In practice, it has been observed that the intended aim and objects have been achieved; in particular, it should be noted that the apparatus according to the invention allows to perform a substantially global measurement of the postural geometry of a patient.

It is also evident, from the above description, that this evaluation of the postural geometry can be as thorough, in terms of measured data level, as desired and required by the operator; an essentially unlimited number of auxiliary devices of the apparatus according to the invention, performing the most disparate measurements, can in fact be mounted substantially at will.

Simplicity in measurement and the possibility, without particular modifications, of interfacing all the measurement devices with transducing and data processing means of the computerized electronic type should also be noted.

In less expensive models, however, postural geometry can be measured also by virtue of mechanical-type transducing and processing means without thereby losing precision and accuracy in measurement.

It should also be noted that the apparatus according to the invention substantially solves definitely the problems related to positioning the patient on devices for measuring anisomelia of the lower limbs.

In particular, it is noted that with the apparatus according to the invention, it is easy to measure postural dysfunctions of the pelvis, especially as regards rotations thereof about the vertical axis and lateral movements thereof, and postural dysfunction of the shoulders, among which mention can be made, for example, of the lowering of one shoulder with respect to the other in addition to translation and rotation.

From the foregoing it is also evident, as regards the anisomelia measurement apparatus, that the replacement of the blocks of foamed plastic material of different densities with pneumatic actuators allows to eliminate the drawbacks observed in the known art.

The use of air for adjusting the system to the loading conditions in fact allows to have both an optimum measurement of anisomelia and to eliminate the need for block replacement which, as mentioned, is currently performed by trial and error.

Furthermore, with this apparatus it is possible, for example for study purposes, to determine forced positions by acting on the patient to control his posture and the consequent difference produced by the intervention (this direct action on the patient was hitherto impossible).

The present invention is susceptible of numerous modifications and variations, all of which are within the scope of the inventive concept; thus, for example, transducers of the electric or electromechanical type, such as potentiometers, can be replaced with transducers of the mechanical type provided with a graduated rod.

All the details may furthermore be replaced with other technically equivalent elements.

The materials, as well as the dimensions, may be any according to the requirements.

What is claimed is:

1. A biomedical apparatus, particularly for measuring anisomelia of the lower limbs of a patient and the posture of the trunk of the patient in relation to the measured anisomelia, comprising:

at least one first post extending vertically from an apparatus for evaluating the anisomelia of the lower limbs;

at least one postural geometry measurement device slidingly coupled to said post;

wherein said apparatus for evaluating the anisomelia of the lower limbs comprises a footing;

a first and second foot resting supports arranged over said footing and each formed by a first and second frame arranged one over the other and hinged together;

a first pneumatic actuator arranged between said footing and said second frame;

a second pneumatic actuator arranged between said footing and said first frame; and a pneumatic locking piston and a potentiometer, both arranged between said footing and said second frame;

a platform being fixed on said first frame, the first pneumatic actuator of each of the second frames being supplied with a same internal pressure value, said second pneumatic actuator being adapted to define a rotation degree of said first frame with respect to said second frame.

2. The apparatus according to claim 1, wherein at least one of said first and second pneumatic actuators of one platform is supplied so as to have the same internal pressure value as at least one of said first and second actuators of the other platform.

3. The apparatus according to claim 1, wherein said platforms have, on a foot resting surface, locator graduations for the degree of divarication of the feet and heel units for exactly positioning said feet.

4. The apparatus according to claim 1, wherein said second pneumatic actuator of each first frame is adapted to move said first frame about a transverse horizontal axis, with respect to said second frame, according to a chosen rotation degree.

5. The apparatus according to claim 1, wherein said first frame and said second frame are slideable on at least one slider along at least one self-aligning ballscrew guide.

6. The apparatus according to claim 1, wherein said at least one measurement device comprises translatory motion means for moving said measurement device at right angles to said at least one first post and so as to match the front/back orientation of the patient.

7. The apparatus according to claim 6, wherein said at least one measurement device comprises a first rod-like element that is slidingly supported by said translatory motion means, the translatory motion of said first rod-like element occurring in a direction that lies at right angles both to said at least one first post and to the direction of the translatory motion of said translatory motion means.

8. The apparatus according to claim 7, wherein a median region of a second rod-like element is rotatably coupled to said first rod-like element at its median region and can oscillate on a plane that is perpendicular to said at least one first post, and is rotatably coupled to said first rod-like element with a vertical rotation axis.

9. The apparatus according to claim 8, wherein terminal portions of two arms are slidingly coupled to said one second rod-like element, said two arms being movable at right angles to the direction of their longitudinal extension and on a plane that coincides with, or is parallel to, an oscillation plane of said second rod-like element.

10. The apparatus according to claim 8, wherein said two arms have mutual sliding motions that are interlinked, the motion of one arm being matched by a symmetrical motion of the other arm.

11. The apparatus according to claim 9, wherein a means for evaluating a difference in height of the shoulders of a patient is slidingly coupled to a free terminal portion of one of said arms.

12. The apparatus according to claim 11, wherein said means for evaluating the difference in height of the shoulders comprises, on one of the free terminal portions of said arms, a third rod-like element comprising a ring with a gear fixed to a stem of a potentiometer that is inserted in the arm.

13. The apparatus according to claim 8, further comprising means for locking said second rod-like element.

14. The apparatus according to claim 1, further comprising a second post that slidingly supports means for measuring the shape of the spinal column.

15. The apparatus according to claim 14, wherein said means for measuring the shape of the spinal column comprise a pantograph.

16. The apparatus according to claim 11, comprising two devices for measuring postural geometry of the patient, one device being dedicated to the measurement of shoulder level differences and of translations and rotations thereof, the other device being dedicated to the measurement of the postural geometry of the pelvis and of translations and rotations thereof.

* * * * *